United States Patent [19]
Obijeski et al.

[11] Patent Number: 5,472,775
[45] Date of Patent: Dec. 5, 1995

[54] ELASTIC MATERIALS AND ARTICLES THEREFROM

[75] Inventors: Todd J. Obijeski, Houston; Georgia M. Huff, Lake Jackson; Rexford A. Maugans, Lake Jackson; Osborne K. McKinney, Lake Jackson, all of Tex.

[73] Assignee: The Dow Chemical Company, Midland, Mich.

[21] Appl. No.: 108,019

[22] Filed: Aug. 17, 1993

[51] Int. Cl.$^6$ .................................................. B32B 33/00
[52] U.S. Cl. ................ 428/220; 428/332; 428/411.1; 428/500; 428/521; 428/523; 428/230; 428/231
[58] Field of Search ............................ 428/220, 219, 428/230, 231, 411.1, 500, 521, 523, 332; 526/348.1, 348

[56] References Cited

U.S. PATENT DOCUMENTS

| | | | |
|---|---|---|---|
| 2,957,512 | 10/1960 | Wade et al. | 156/163 |
| 3,156,242 | 3/1962 | Crowe, Jr. | 128/96.1 |
| 3,645,992 | 2/1972 | Elston | 526/169.2 |
| 3,678,134 | 7/1972 | Middlebrook | 525/98 |
| 3,849,241 | 11/1974 | Butin et al. | 428/137 |
| 3,881,489 | 5/1975 | Hartwell | 128/287 |
| 3,949,128 | 4/1976 | Ostermeier | 428/152 |
| 3,989,867 | 11/1976 | Sisson | 428/132 |
| 4,076,698 | 2/1978 | Anderson et al. | 526/348.6 |

(List continued on next page.)

FOREIGN PATENT DOCUMENTS

| | | |
|---|---|---|
| 2085073 | 6/1993 | Canada . |
| 0546837 | 6/1993 | European Pat. Off. . |
| 93/08221 | 4/1993 | WIPO . |
| 94/06857 | 3/1994 | WIPO . |
| 94/07930 | 4/1994 | WIPO . |
| 94/18263 | 8/1994 | WIPO . |
| 94/28064 | 12/1994 | WIPO . |

OTHER PUBLICATIONS

International Search Report dated Oct. 19, 1994 issued by the EPO acting as the International Searching Authority in PCT/US94/08374.

J. C. Randall, "Characterization of Long–Chain Branching in Polyethylenes Using High Field Carbon–13 NMR," ACS Symposium Series No. 142, pp. 93–118 (1980).

M. Shida et al., "Correlation of Low Density Polyethylene Rheological Measurements with Optical and Processing Properties", *Polymer Engineering Science*, vol. 17, No. 11, pp. 769–774 (1977).

John Dealy, *Rheometers for Molten Plastics*, Van Nostrand Co., pp. 97–99 (1982).

"INSITE™ Technology Polyolefins (ITP)–New Rules in the Structure/Rheology Relationship of Ethylene α–Olefin Copolymers", *ANTEC '93 Proceedings*, New Orleans, La., pp. 1188–1192 (May 1993).

Ramamurthy, "Wall Slip in Viscous Fluids and Influence of Materials of Construction", *Journal of Rhelogy*, V. 30(2), pp. 337–357 (1986).

Wild et al., "Determination of Branching Distributions in Polyethylene and Ethylene Copolymer", *Journal of Polymer Science, Poly Phys. Ed.*, vol. 20, pp. 441–455 (1982).

*The Encyclopedia of Chemical Technology, Kirk–Othmer*, Third Edition, John Wiley & Sons, New York, vol. 16, pp. 415–417 (1981).

(List continued on next page.)

*Primary Examiner*—Patrick J. Ryan
*Assistant Examiner*—Marie R. Macholl

[57] ABSTRACT

Elastic materials, particularly films, strips, coatings, ribbons and sheets made from at least one substantially linear ethylene polymer are disclosed which can be fabricated on conventional polyolefin extrusion equipment. They can be used to produce elastic composite structures that are stretchable and have recycle compatibility between elastic and non-elastic components. The novel materials have at least about 80% recovery at 100% strain and are especially useful in making fabricated composite articles (e.g., disposable diapers).

15 Claims, 2 Drawing Sheets

U.S. PATENT DOCUMENTS

| | | | |
|---|---|---|---|
| 4,181,762 | 1/1980 | Benedyk | 428/97 |
| 4,197,377 | 4/1980 | Bohm et al. | 525/99 |
| 4,250,273 | 2/1981 | Rohm et al. | 525/99 |
| 4,296,163 | 10/1981 | Emi et al. | 428/212 |
| 4,323,534 | 4/1982 | DesMarais | 264/176 R |
| 4,381,781 | 5/1983 | Sciaraffa et al. | 604/372 |
| 4,426,420 | 1/1984 | Likhyani | 428/224 |
| 4,450,026 | 5/1984 | Pieniak et al. | 156/164 |
| 4,479,989 | 10/1984 | Mahal | 428/35 |
| 4,543,099 | 9/1985 | Bunnelle et al. | 604/385 A |
| 4,652,487 | 3/1987 | Morman | 428/138 |
| 4,655,760 | 4/1987 | Morman et al. | 604/385 A |
| 4,657,802 | 4/1987 | Morman | 428/152 |
| 4,663,220 | 5/1987 | Wisneski et al. | 428/221 |
| 4,707,398 | 11/1987 | Boggs | 428/224 |
| 4,719,261 | 1/1988 | Bunnelle et al. | 525/97 |
| 4,720,415 | 1/1988 | Vander Weilen et al. | 428/152 |
| 4,724,184 | 2/1988 | Killian et al. | 428/227 |
| 4,734,311 | 3/1988 | Sokolowski | 428/152 |
| 4,741,949 | 5/1988 | Norman et al. | 428/224 |
| 4,777,080 | 10/1988 | Harris, Jr. et al. | 428/212 |
| 4,781,966 | 11/1988 | Taylor | 428/152 |
| 4,798,081 | 1/1989 | Hazlitt et al. | 23/53 |
| 4,801,482 | 1/1989 | Goggans et al. | 428/68 |
| 4,803,117 | 2/1989 | Daponte | 428/228 |
| 4,818,597 | 4/1989 | DaPonte et al. | 428/284 |
| 4,820,572 | 4/1989 | Killian et al. | 428/227 |
| 4,861,652 | 8/1989 | Lippert et al. | 428/284 |
| 4,863,779 | 9/1989 | Daponte | 428/152 |
| 4,883,549 | 11/1989 | Frost et al. | 156/161 |
| 4,891,957 | 1/1990 | Strack et al. | 66/192 |
| 4,923,742 | 5/1990 | Killian et al. | 428/283 |
| 4,935,287 | 6/1990 | Johnson et al. | 428/198 |
| 4,938,753 | 7/1990 | Van Gompel et al. | 604/385.2 |
| 4,938,757 | 7/1990 | Van Gompel et al. | 604/396 |
| 4,940,464 | 7/1990 | Van Gompel et al. | 604/396 |
| 4,965,122 | 10/1990 | Morman | 428/225 |
| 4,981,747 | 1/1991 | Morman | 428/198 |
| 5,036,551 | 8/1991 | Dailey et al. | 2/167 |
| 5,037,416 | 8/1991 | Allen et al. | 604/385.1 |
| 5,057,097 | 10/1991 | Gesp | 604/389 |
| 5,085,654 | 2/1992 | Buell | 604/370 |
| 5,110,870 | 5/1992 | Fujii et al. | 525/194 |
| 5,116,662 | 5/1992 | Morman | 428/198 |
| 5,169,706 | 12/1992 | Collier, IV et al. | 428/152 |
| 5,196,000 | 3/1993 | Clear et al. | 604/385.2 |
| 5,241,031 | 8/1993 | Mehta | 526/348.1 |
| 5,272,236 | 12/1993 | Lai et al. | 526/348.5 |
| 5,278,272 | 1/1994 | Lai et al. | 526/348.5 |
| 5,326,602 | 7/1994 | Rifi | 428/35.7 |

OTHER PUBLICATIONS

*The Encyclopedia of Chemical Technology,* Kirk–Othmer, Third Edition, John Wiley & Sons, New York, vol. 18, pp. 191–192 (1981).

"Mid–October 1989 Encyclopedia Issue", *Modern Plastics,* vol. 66, No. 11, pp. 242–248 (1989).

Seymour S. Schwartz and Sidney H. Goodman, *Plastics Materials and Processes,* Van Nostrand Reinhard Company, New York, pp. 527–563, pp. 632–647, and pp. 596–602 (1982).

ELASTIC MATERIALS AND ARTICLES THEREFROM

CROSS-REFERENCE TO RELATED APPLICATIONS

This application is related to application Ser. No. 08/053,583, filed Apr. 27, 1993 (now abandoned) application Ser. No. 08/084,054, filed Jun. 29, 1993 (now U.S. Pat. No. 5,395,471). U.S. Pat. No. 5,272,236; pending application Ser. No. 08/055,063, filed Apr. 28, 1993; and U.S. Pat. No. 5,278,272, the disclosures of all of which are incorporated herein by reference.

1. Field of the Invention

This invention relates to elastic materials, particularly, elastic films, strips, sheets and composites, and to articles fabricated therefrom, such as disposable incontinence garments or diapers. The elastic materials comprise at least one judiciously selected homogeneously branched substantially linear ethylene polymer.

2. Background of the Invention

Materials with excellent stretchability and elasticity are needed to manufacture a variety of disposable and durable articles, such as incontinence garments, disposable diapers and furniture upholstery. Stretchability and elasticity are desirable characteristics to effectuate a closely conforming fit to the body of the wearer or to the frame of the item. It is also desirable to maintain the conforming fit during repeated use, extensions and retractions. For incontinence articles, stretchability and elasticity are particularly desirable to insure comfort and provide security against unwanted leaks.

Disposable articles are typically prepared by the combination of polymer fibers, films, sheets and absorbent materials. Whereas the fibers are prepared by well known processes such as spunbonding, melt blown and continuous filament wounding, the film and sheet forming processes typically involve known extrusion and coextrusion processes, e.g., blown bubble extrusion, extrusion casting, profile extrusion, injection molding, extrusion coating and extrusion sheet. The resultant elastic film, coating or sheet may be subsequently cut or slit to short lengths and/or narrow widths to prepare strips, tapes, bands, ribbons or the like.

There are at least two ways elastic materials are employed to manufacture disposable and durable articles. Elastic films, strips and sheets are used as uncombined elastic components (panels or portions), or they are constructed as or into multilayer structures to provide elastic composite materials with enhanced elasticity and stretchability. In a diaper, for example, experimental and commercial uses include in or as side panels, waist bands, backsheets, leg bands, and even topsheets where the elastic material is rendered pervious or "breathable" by such methods as aperturing, slitting, or microperforating as suggested by Lippert et al. in U.S. Pat. No. 4,861,652 (the disclosure of which is incorporated herein by reference).

An example of the use of elastic materials to construct elastic composite materials is provided by Van Gompel et al. in U.S. Pat. Nos. 4,940,464, 4,938,757 and 4,938,753 (the disclosures of all of which are incorporated herein by reference). Van Gompel et at. disclose disposable incontinence garments containing elastic gathering means and stretchable side panels. The gathering means and stretchable side panels are made from film of block or graft copolymers such as butadiene, isoprene, styrene, ethylene-methyl acrylate, ethylene-vinyl acetate, ethylene-ethyl acrylate or blends thereof.

An example of use of elastic materials to construct composites with the particular benefit of enhanced stretchability is a stretchable fastening tape for a disposable diaper disclosed by Gesp in U.S. Pat. No. 5,057,097, the disclosure of which is incorporated herein by reference.

There has been a persistent need for extrudable materials suitable for producing films, strips, sheets and composites with excellent stretchability and elasticity. Although there are a variety of elastic materials currently available, these known solutions require blending or additive incorporation to meet desire levels of extrusion processability, stretchability or elasticity. Still other proposed solutions such as the method disclosed by Butin in U.S. Pat. No. 3,849,241, the disclosure of which is incorporated herein by reference, require "controlled thermal and oxidative degradation" of the elastic material to affect viscosity adjustments prior to extrusion. Yet other prior art solutions, such as the disclosure by de Marais in U.S. Pat. No. 4,323,534 (incorporated herein by reference), requires a post-extrusion leaching step to extract processing aids such as fatty acid amides. Moreover, prior art elastic materials generally involve expensive elastomers such as styrene butadiene copolymers, polyether block amides, polyether esters and polyurethanes which typically necessitate blending with polyolefins for adequate extrusion processability.

Where polyolefins themselves have been previously employed as elastic materials, other problems have arisen. For example, where ethylene/$\alpha,\beta$-unsaturated copolymers are known to possess improved elasticity as a function of increased comonomer levels, Daponte in U.S. Pat. No. 4,803,117, the disclosure of which is incorporated herein by reference, discloses ethylene vinyl ester copolymers with high vinyl ester levels are requisite to effectuate adequate elasticity for disposable articles. However, these high vinyl ester levels invariably renders the polymer susceptible to undue thermal degradation.

Definitions

Several definitions have been adopted herein as previously described by Collier et al. in U.S. Pat. No. 5,169,706, the disclosure of which is incorporated herein by reference. The term "elastic" means that the film will recover at least about 50 percent of its stretched length after the first pull and after the fourth pull to 100% strain (doubled the length). Elasticity can also be described by the "permanent set" of the film. Permanent set is the converse of elasticity. A film is stretched to a certain point and subsequently released to the original position before stretch, and then stretched again. The point at which the elastic material begins to pull a load is designated as the percent permanent set.

The term "stretchable" is used herein in reference any material which, upon application of a biasing force, elongates at least about 60 percent (i.e., to a stretched, biased length which is at least about 160 percent of its relaxed unbiased length), and which, will recover at least 55 percent of its elongation upon release of the stretching, elongating force. A hypothetical example would be a one (1) inch sample of a material which is elongated or stretched to at least 1.60 inches and which, upon being elongated to 1.60 inches and released, will recover to a length of not more than 1.27 inches. Many elastic materials maybe elongated by much more than 60 percent (i.e., much more than 160 percent of their relaxed length), for example, elongated 100 percent or more, and many of these will recover to substantially their initial relaxed length, for example, to within 105 percent of their original relaxed length, upon release of the stretching force.

As used herein, the terms "recover" and "recovery" refer to a contraction of a stretched material upon termination of a biasing force following stretching of the material by application of the biasing force. For example, if a material having a relaxed, unbiased length of one (1) inch is elongated 50 percent by stretching to a length of one and one half (1.5) inches the material would be elongated 50 percent (0.5 inch) and would have a stretched length that is 150 percent of its relaxed length. If this exemplary stretched material contracted, that is recovered to a length of one and one tenth (1.1) inches after release of the biasing and stretching force, the material would have recovered 80 percent (0.4 inch) of its one-half (0.5) inch elongation. Recovery may be expressed as [(maximum stretch length—final sample length)/(maximum stretch length—initial sample length)]× 100.

As used herein, the term "nonelastic" refers to any material which does not fall within the definition of "elastic" or "stretchable" above.

As used herein, the term "less-elastic" includes "nonelastic" and any material referenced apposite an "elastic material".

The term "elastic material" as used herein refers to the films, strips, coatings, tapes, webs, ribbons, bands, sheets and the like as well as the "elastic composite materials" disclosed herein unless specifically distinguished as pertaining to the prior art.

The term "elastic composite material" as used herein refers to a multilayer material (including a fabric) having at least one elastic material layer joined to at least one less-elastic layer at least at two locations in which the less-elastic layer is extended or gathered between the locations where it is joined to the elastic layer. A elastic composite material may be stretched to the extent that the less-elastic material between the bond locations allows the elastic material to elongate or stretch. An example of this type of elastic composite material is disclosed, for example, by U.S. Pat. No. 4,720,415 to Vander Wielen et al., issued Jan. 19, 1988, which is hereby incorporated by reference.

The term "article" as used herein refers to fabricated composite items comprising elastic materials disclosed herein. Articles include disposable infant care and adult incontinence care items such as incontinence garments, training pants and diapers.

The term "stretch-to-end" as used herein refers to a ratio determined from the difference between the unextended dimension of a composite elastic material and the maximum extended dimension of a composite elastic material (i.e., additional extension would rupture bonds which connecting individual layers or components of the composite together) and dividing that difference by the unextended dimension of the composite elastic material. If the stretch-to-end is expressed as a percentage, this ratio is multiplied by 100. For example, a composite elastic material having an unextended length of 5 inches and a maximum extended length of 10 inches, has a stretch-to-end of 100 percent. Stretch-to-end may also be referred to in prior art as "maximum nondestructive elongation".

As used in the claims herein, the term "consisting essentially of" means that the substantially linear ethylene polymers used to make the elastic materials can have additional materials which do not materially affect its elasticity.

The terms "homogeneous branching distribution" and "homogeneously branched" are defined herein to mean that (1) the α-olefin comonomer is randomly distributed within a given molecule, (2) substantially all of the copolymer molecules have the same ethylene-to-comonomer ratio, (3) the polymer is characterized by a narrow short chain branching distribution where the short chain branching index (defined herein below) is greater than 30 percent, more preferably greater than 50 percent, and (4) the polymer essentially lacks a measurable high density (crystalline) polymer fraction as measured by known fractionation techniques such as, for example, a method that involves polymer fractional elutions as a function of temperature.

The term "interpolymer" is used herein to indicate a copolymer, or a terpolymer, or the like, where, at least one other comonomer is polymerized with ethylene to make the interpolymer.

The term "substantially linear" means that the polymer backbone is substituted with about 0.01 long chain branch/ 1000 carbons to about 3 long chain branches/1000 carbons, more preferably from about 0.01 long chain branch/1000 carbons to about 1 long chain branch/1000 carbons, and especially from about 0.05 long chain branch/1000 carbons to about 1 long chain branch/1000 carbons.

The term "long chain branching" is defined herein as a chain length of at least about 6 carbons, above which the length cannot be distinguished using $^{13}$C nuclear magnetic resonance spectroscopy, yet the long chain branch can be about the same length as the length of the polymer backbone.

Long chain branching is determined by using $^{13}$C nuclear magnetic resonance (NMR) spectroscopy and is quantified using the method described by Randall (*Rev. Macromol. Chem. Phys.*, C29, V. 2&3, p. 285–297), the disclosure of which is incorporated herein by reference.

SUMMARY OF THE INVENTION

We have discovered new elastic materials which do not need additives to be elastic. These new elastic films, strips, coatings, ribbons and sheets can be produced on conventional extrusion equipment (e.g., blown bubble, extrusion casting, extrusion coating and sheet extrusion) and they can be used to produce highly elastic composites whereby there is excellent recycle compatibility between the elastic and less-elastic components of fabricated disposable articles, particularly when the article comprises only polyolefin materials and absorbent hydrogel materials such as polyacrylic acid supplied.

Preparation of the elastic materials disclosed herein does not involve "controlled degradation" prior to extrusion, or a post-extrusion additive extraction step, nor do these elastic materials show any particular susceptibility to undo thermal degradation.

These elastic materials are made from unique elastic homogeneously branched substantially linear ethylene polymers which exhibit extrusion processability characteristics that are substantially improved in contrast to heterogeneously branched linear low density polyethylene. The benefit of improved processability is manifested on conventional polyolefin extrusion equipment as higher extrusion outputs (productivity) and/or as lower die pressure and extruder amperage (energy consumption).

The new elastic materials of the present invention have permanent set values of about 20% or less, or, stated another way, percent recovery values of at least about 80%. This property is surprisingly different than the response of films, strips, coatings and sheets made from other polyolefins which are known to vary predictably as a function of polymer density or crystallinity wherein higher density or crystallinity yields higher percent permanent set values characteristic of the material being less-elastic or nonelastic. Surprisingly, the elastic substantially linear ethylene polymers disclosed herein are distinguished from other substantially linear ethylene polymers by their tendency to show enhanced elasticity as film thickness decreases while other substantially linear ethylene polymers with the polymer densities greater than about 0.89 g/cm³ tend to show equivalent or less elasticity at reduced film thicknesses. The new elastic materials disclosed herein are made from at least one homogeneously branched substantially linear ethylene polymer having:

a) a melt flow ratio, $I_{10}/I_2$, $\geq 5.63$, b) a molecular weight distribution, $M_w/M_n$, defined by the equation:

$$M_w/M_n \leq (I_{10}/I_2) - 4.63,$$

c) a critical shear rate at onset of surface melt fracture of at least 50 percent greater than the critical shear rate at the onset of surface melt fracture of a linear ethylene polymer having about the same $I_2$ and $M_w/M_n$, and d) a density less than about 0.89 g/cm³.

DESCRIPTION OF THE PREFERRED EMBODIMENTS

Substantially Linear Ethylene Polymers

The substantially linear ethylene polymers used in the present invention are a unique class of compounds that are further defined in application Ser. No. 07/776,130 filed Oct. 15, 1991 (now U.S. Pat. No. 5,272,236) and in application Ser. No. 07/939,281 filed Sep. 2, 1992 (now U.S. Pat. No. 5,278,272), the teachings of all of which are incorporated herein by reference. The teachings disclosed in these copending applications include the utilization of constrained geometry catalysts and suitable methods of production.

The homogeneously branched substantially linear ethylene polymers are characterized as having:

a) a melt flow ratio, $I_{10}/I_2$, $\geq 5.63$, b) a molecular weight distribution, $M_w/M_n$, defined by the equation:

$$M_w/M_n \leq (I_{10}/I_2) - 4.63,$$

and c) a critical shear stress at onset of gross melt fracture greater than $4 \times 10^6$ dyne/cm².

The homogeneously branched substantially linear ethylene polymers can also be characterized as having:

a) a melt flow ratio, $I_{10}/I_2$, $\geq 5.63$, b) a molecular weight distribution, $M_w/M_n$, defined by the equation:

$$M_w/M_n \leq (I_{10}/I_2) - 4.63,$$

and c) a critical shear rate at onset of surface melt fracture at least 50 percent greater than the critical shear rate at the onset of surface melt fracture of either a homogeneously or heterogeneously branched linear ethylene polymer having about the same $I_2$ and $M_w/M_n$.

The unique homogeneously branched substantially linear ethylene polymers used to make the elastic materials are easily distinguished from homogeneously branched linear ethylene polymers. The term "homogeneously branched linear ethylene polymer" means that the polymer does not have long chain branching. That is, the linear ethylene polymer has an absence of long chain branching, as for example the traditional heterogeneously branched linear low density polyethylene polymers or linear high density polyethylene polymers made using Ziegler polymerization processes (e.g., U.S. Pat. No. 4,076,698 (Anderson et al.) the disclosure of which is incorporated herein by reference) or linear homogeneously branched polymers (e.g., U.S. Pat. No. 3,645,992 (Elston) the disclosure of which is incorporated herein by reference). The term "linear ethylene polymers" does not refer to high pressure branched polyethylene, ethylene/vinyl acetate copolymers, ethylene/acrylic acid copolymers, or ethylene/vinyl alcohol copolymers which are known to those skilled in the art to have numerous long chain branches.

The homogeneously branched substantially linear ethylene polymers used to form the elastic film, strips, coatings, ribbons and sheets of the present invention have homogeneous branching distributions and a single melting peak, as measured using differential scanning calorimetry (DSC), in contrast to heterogeneously branched linear ethylene polymers, which have 2 or more melting peaks, due to the heterogeneously branched polymer's broad short chain branching distribution.

A unique characteristic of the homogeneously branched substantially linear ethylene polymers used to prepare the elastic films, strips, coatings, ribbons and sheets of this invention is a highly unexpected flow property where the $I_{10}/I_2$ value of the polymer is essentially independent of polydispersity index (i.e. $M_w/M_n$) of the polymer. This is contrasted with conventional linear homogeneously branched and linear heterogeneously branched polyethylene resins having rheological properties such that to increase the $I_{10}/I_2$ value, the polydispersity index must also be increased. In addition, the unique homogeneously branched substantially linear ethylene polymers of this invention also exhibit enhanced processability as manifested by a higher extrusion output, lower pressure drop through screen packs and gel filters, lower extruder amperage and lower die pressure.

Suitable unsaturated comonomers useful for polymerizing with ethylene to prepare the elastic materials of this invention include, for example, ethylenically unsaturated monomers, conjugated or non-conjugated dienes, polyenes, etc.

Examples of such comonomers include $C_3$–$C_{20}$ α-olefins as propylene, isobutylene, 1-butene, 1-hexene, 4-methyl-1-pentene, 1-heptene, 1-octene, 1-nonene, 1-decene, and the like. Preferred comonomers include propylene, 1-butene, 1-hexene, 4-methyl-1-pentene and 1-octene, and 1-octene is especially preferred. Other suitable monomers include styrene, halo- or alkyl-substituted styrenes, tetrafluoroethylene, vinylbenzocyclobutane, 1,4-hexadiene, 1,7-octadiene, and cycloalkenes, e.g., cyclopentene, cyclohexene and cyclooctene.

The density of the homogeneously branched substantially linear ethylene polymers used to make the elastic materials of the present invention is measured in accordance with ASTM D-792 and is generally less than about 0.89 g/cm$^3$, preferably from about 0.85 g/cm$^3$ to about 0.89 g/cm$^3$, and especially from about 0.85 g/cm$^3$ to about 0.88 g/cm$^3$.

Molecular Weight

The molecular weight of the substantially linear ethylene interpolymers is conveniently indicated using a melt index measurement according to ASTM D-1238, Condition 190 C/2.16 kilogram (kg), formerly known as "Condition E" and also known as $I_2$. Melt index is inversely proportional to the molecular weight of the polymer. Thus, the higher the molecular weight, the lower the melt index, although the relationship is not linear. The melt index for the substantially linear ethylene interpolymers useful herein is generally from about 0.01 gram/10 minutes (g/10 min.) to about 30 g/10 min., preferably from about 0.1 g/10 min. to about 20 g/10 min., and especially from about 0.5 g/10 min. to about 15 g/10 min.

Other measurements useful in characterizing the molecular weight of substantially linear ethylene polymers involve melt index determinations with higher weights, such as, for common example, ASTM D-1238, Condition 190 C/10 kg (formerly known as "Condition N" and also known as $I_{10}$). "Melt flow ratio" is defined herein as the ratio of a higher weight melt index determination to a lower weight melt index determination, and for measured $I_{10}$ and the $I_2$ melt index values, the melt flow ratio is conveniently designated as $I_{10}/I_2$.

Unlike heterogeneous conventional linear polymers which possess no substantial long chain branching, for the substantially linear ethylene polymers used to prepare the elastic films, strip, coatings, ribbons and sheets and elastic composite structures of the present invention, the melt flow ratio actually indicates the degree of long chain branching, i.e., the higher the $I_{10}/I_2$ melt flow ratio, the more long chain branching in the polymer. The $I_{10}/I_2$ ratio of the substantially linear ethylene polymers is at least about 5.63, preferably at least about 6, and more preferably at least about 6.5. Generally, the upper limit of $I_{10}/I_2$ ratio for the homogeneous branched substantially linear ethylene polymers is about 50 or less, preferably about 30 or less, and especially about 20 or less.

Molecular Weight Distribution

The substantially linear ethylene polymers are analyzed by gel permeation chromatography (GPC) on a Waters 150 high temperature chromatographic unit equipped with differential refractometer and three columns of mixed porosity. The columns are supplied by Polymer Laboratories and are commonly packed with pore sizes of 10$^3$, 10$^4$, 10$^5$ and 10$^6$ Å. The solvent is 1,2,4-trichlorobenzene, from which 0.3 percent by weight solutions of the samples are prepared for injection. The flow rate is 1.0 milliliters/minute and the operating temperature is 140 C with a 100-microliter injection size.

The molecular weight determination with respect to the polymer backbone is deduced by using narrow molecular weight distribution polystyrene standards (from Polymer Laboratories) in conjunction with their elution volumes. The equivalent polyethylene molecular weights are determined by using appropriate Mark-Houwink coefficients for polyethylene and polystyrene (as described by Williams and Ward in *Journal of Polymer Science*, Polymer Letters, Vol. 6, p. 621, 1968, incorporated herein by reference) to derive the following equation:

$$M_{polyethylene} = a * (M_{polystyrene})^b.$$

In this equation, a=0.4316 and b=1.0. Weight average molecular weight, $M_w$, is calculated in the usual manner according to the following formula: Mw=R $w_i$* $M_i$, where $w_i$ and $M_i$ are the weight fraction and molecular weight, respectively, of the i$^{th}$ fraction eluting from the GPC column.

The $M_w/M_n$ of the substantially linear homogeneously branched ethylene polymers is defined by the equation:

$$M_w/M_n \leq (I_{10}/I_2) - 4.63.$$

Preferably, the $M_w/M_n$ is from about 1.5 to about 2.5, and especially about 2.

The homogeneously branched substantially linear ethylene polymers can, however, have varying $I_{10}/I_2$ ratios due to long chain branch incorporation, while maintaining a low molecular weight distribution (i.e., $M_w/M_n$ from about 1.5 to about 2.5).

Rheological Characteristics

The "rheological processing index" (PI) which is defined herein as the apparent viscosity in kpoise of a polymer measured by a gas extrusion rheometer (GER), can also be used to distinguish the substantially linear ethylene polymers of this invention. The gas extrusion rheometer is described by M. Shida, R. N. Shroff and L. V. Cancio in *Polymer Engineering Science*, Vol. 17, No. 11, p. 770 (1977), and in "Rheometers for Molten Plastics" by John Dealy, published by Van Nostrand Reinhold Co. (1982) on pp. 97–99, both publications of which are incorporated by reference herein in their entirety. GER experiments are performed at a temperature of 190° C., at nitrogen pressures between 250 to 5500 psig (17–379 bars) using about a 7.54 cm diameter, 20:1 L/D die with an entrance angle of 180°. For the substantially linear ethylene polymers described herein, the PI is the apparent viscosity (in kpoise) of a material measured by GER at an apparent shear stress of 2.15×10$^6$ dyne/cm$^2$ and is determined from the following equation:

$$PI = 2.15 \times 10^6 \text{ dynes/cm}^2/(1000 \times \text{shear rate}),$$

where:

2.15×10$^6$ dynes/cm$^2$ is the shear stress at 2500 psi, and the shear rate is the shear rate at the wall as represented by the following equation:

$$32 \ Q'/(60 \text{ sec/min})(0.745)(\text{Diameter} \times 2.54 \text{ cm/in})^3,$$

where:

Q' is the extrusion rate (gms/min), 0.745 is the melt density of polyethylene (gm/cm$^3$), and Diameter is the orifice diameter of the capillary (in.).

The unique substantially linear ethylene interpolymers described herein preferably have a PI in the range of about 0.01 kpoise to about 50 kpoise, preferably about 15 kpoise or less. The unique substantially linear ethylene interpolymers and homopolymers described herein have a PI less than or equal to about 70% of the PI of a comparative linear ethylene polymer (either a Ziegler polymerized polymer or a linear uniformly branched polymer as described by Elston in U.S. Pat. No. 3,645,992) at about the same $I_2$ and $M_w/M_n$.

To more fully characterize the rheological behavior of the unique substantially linear ethylene polymers, S. Lai and G. W. Knight recently introduced (*ANTEC '93 Proceedings*, INSITE™ Technology Polyolefins (ITP)–New Rules in the Structure/Rheology Relationship of Ethylene α-Olefin Copolymers, New Orleans, La., May 1993) another rheological measurement, the Dow Rheology Index (DRI), which expresses a polymer's "normalized relaxation time as the result of long chain branching." DRI ranges from 0 for polymers which do not have any measurable long chain branching (e.g., Tafmer™ products supplied by Mitsui and Exact™ products supplied by Exxon) to about 15 and is independent of melt index. In general, for low to medium pressure ethylene polymers (particularly at lower densities) DRI provides improved correlations to melt elasticity and high shear flowability relative to correlations of the same attempted with melt flow ratios, and for the substantially linear ethylene polymers of this invention, DRI is preferably at least about 0.1, and especially at least about 0.5, and most especially at least 0.8. DRI can be calculated from the equation:

$$DRI=(3652879*\tau_o^{1.00649}/\eta_o-1)/10$$

where $\tau_o$ is the characteristic relaxation time of the material and $\eta_o$ is the zero shear viscosity of the material. Both $\tau_o$ and $\eta_o$ are the "best fit" values to the Cross equation, i.e.

$$\eta/\eta_o=1/(1+(\gamma*\eta_o)^{1-n})$$

where n is the power law index of the material, and $\eta$ and $\gamma$ are the measured viscosity and shear rate, respectively. Baseline determination of viscosity and shear rate data are obtained using a Rheometric Mechanical Spectrometer (RMS-800) under dynamic sweep mode from 0.1 to 100 radians/second at 160 C and a Gas Extrusion Rheometer (GER) at extrusion pressures from 1,000 psi to 5,000 psi (corresponding shear stress from 0.086 to 0.43 MPa) using a 7.54 centimeter diameter, 20:1 L/D die at 190 C. Specific material determinations can be performed from 140 to 190 C as required to accommodate melt index variations.

Additionally, ethylene polymers can also be distinguished by melt flow consequences that are manifested as solid state surface defects such as "melt fracture". An apparent shear stress versus apparent shear rate plot is used to identify the "melt fracture" phenomena which pertains to surface irregularities. According to Ramamurthy in the *Journal of Rheology*, 30(2), 337–357, 1986, above a certain critical shear rate (in contrast to a critical draw rate for the draw resonance phenomena), the observed extrudate irregularities may be broadly classified into two main types: surface melt fracture and gross melt fracture.

Surface melt fracture occurs under apparently steady flow conditions and ranges in detail from loss of specular film gloss to the more severe form of "sharkskin." In this disclosure, the onset of surface melt fracture (OSMF) is characterized at the beginning of losing extrudate gloss at which the surface roughness of the extrudate can only be detected by 40× magnification. The critical shear rate at the onset of surface melt fracture for the substantially linear ethylene polymers is at least 50 percent greater than the critical shear rate at the onset of surface melt fracture of a comparative linear ethylene polymer (either a Ziegler polymerized polymer or a linear homogeneously branched polymer as described by Elston in U.S. Pat. No. 3,645,992) having about the same $I_2$ and $M_w/M_n$.

Gross melt fracture occurs at unsteady extrusion flow conditions, and ranges in detail from regular (alternating rough and smooth, helical, etc.) to random distortions. For commercial acceptability, surface defects should be minimal, if not absent, for good film, coating or sheet quality and properties. The critical shear stress at the onset of gross melt fracture for the substantially linear ethylene polymers used in the present invention is greater than about $4\times10^6$ dynes/cm$^2$. The critical shear rate at the onset of surface melt fracture (OSMF) and the onset of gross melt fracture (OGMF) will be used herein based on the changes of surface roughness and configurations of the extrudates extruded by a GER.

Short Chain Branching

The distribution of comonomer branches for substantially linear ethylene polymers is characterized by its SCBDI (Short Chain Branch Distribution Index) or CDBI (Composition Distribution Branch Index) and is defined as the weight percent of the polymer molecules having a comonomer content within 50 percent of the median total molar comonomer content. The CDBI of a polymer is readily calculated from data obtained from techniques known in the art, such as, for example, temperature rising elution fractionation (abbreviated herein as "TREF") as described, for example, by Wild et al., *Journal of Polymer Science, Poly. phys. Ed.*, Vol. 20, p. 441 (1982), or in U.S. Pat. No. 4,798,081, both disclosures of which are incorporated herein by reference. The SCBDI or CDBI for the substantially linear interpolymers of the present invention is preferably greater than about 30 percent, especially greater than about 50 percent.

The substantially linear ethylene interpolymers used in this invention essentially lack a measurable "high density" fraction as measured by the TREF technique. The substantially linear polymers do not contain a polymer fraction with a degree of branching less than or equal to 2 methyls/1000 carbons. The "high density polymer fraction" can also be described as a polymer fraction with a degree of branching less than about 2 methyls/1000 carbons. One of the chief benefits of the lack of high density polymer fraction is polymer materials with improved stretchability and elasticity.

Additional Embodiments

Additives such as antioxidants (e.g., hindered phenolics such as Irganox® 1010 or Irganox® 1076 supplied by Ciba Geigy), phosphites (e.g., Irgafos® 168 also supplied by Ciba Geigy), cling additives (e.g., PIB), Standostab PEPQ™ (supplied by Sandoz), pigments, colorants, fillers, and the like, although not required to achieve the desired results of this invention, can also be included in the elastic materials disclosed herein. However, the additives should incorporated in such manners or to the extent that they do not interfere with the enhanced elasticity and stretchability discovered by Applicants. The elastic films, strips, coatings, tapes, ribbons and sheets may also contain additives to enhance antiblocking and coefficient of friction characteristics. Still other additives, such as surfactants and quaternary ammonium compounds alone or in combination with ethylene-acrylic acid (EAA) copolymers or other functional polymers, may also be added to effectuate desired wetting, antistatic or antimicrobial characteristics and the like of the elastic materials and elastic composite structures of this invention.

Similar to the use of additives and although not required to gain the benefits of the present invention, the substantially linear ethylene polymers disclosed herein can be admixed with other polymers to modify characteristics such as elasticity, processability, strength, thermal bonding, or adhesion, to the extent that such modification does not adversely affect the enhanced properties discovered by the Applicants.

Some useful materials for modifying the substantially linear ethylene interpolymers of this invention include, other substantially linear ethylene polymers as well as other polyolefins, such as high pressure low density ethylene homopolymer (LDPE), ethylene-vinyl acetate copolymer (EVA), ethylene-carboxylic acid copolymers, ethylene acrylate copolymers, polybutylene (PB), ethylene/α-olefin polymers which includes high density polyethylene (HDPE), medium density polyethylene, polypropylene, ethylene-propylene interpolymers, linear low density polyethylene (LLDPE), ultra low density polyethylene (ULDPE), as well as graft-modified polymers involving, for example, anhydrides and/or dienes, or mixtures thereof.

Still other polymers suitable for modifying the substantially linear polymers of the present invention include synthetic and natural elastomers and rubbers which are known to exhibit varying degrees of elasticity. AB and ABA block or graft copolymers (where A is a thermoplastic endblock such as, for example, a styrenic moiety and B is an elastomeric midblock derived, for example, from conjugated dienes or lower alkenes), chlorinated elastomers and rubbers, ethylene propylene diene monomer (EDPM) rubbers, ethylene-propylene rubbers, and the like and mixtures thereof are examples of known prior art elastic materials contemplated as suitable for modifying the elastic materials disclosed herein.

For the elastic composite materials of the present invention, any layer (or portion) and any No. of layers can comprise at least one substantially linear ethylene polymer. However, preferably, the elastic material disclosed herein comprises at least 10 weight percent of any mixture or composite.

Elastic Material

Figure 1:
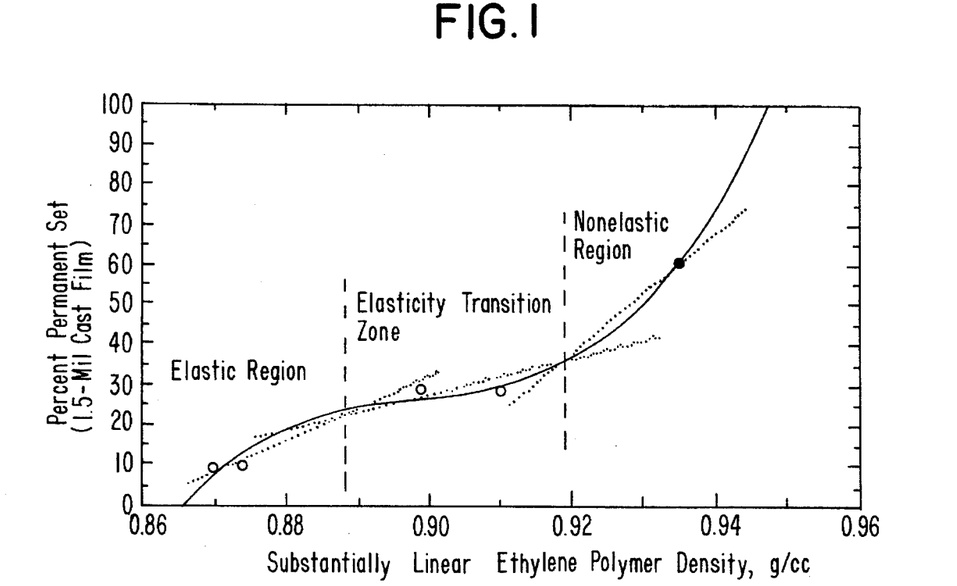
FIG. 1 graphically displays percent permanent set for 1.5 mil film made from elastic substantially linear ethylene polymers of the present invention versus the density of the polymer as well as three assigned regions of relative elasticity. The curve fit is the result of computergenerated third order polynominal regression analysis and the region assignments are the result of discernible and substantial slope changes within those regions.

The materials claimed herein are elastic. For the homogeneously branched substantially linear ethylene polymers used herein, the percent permanent set relates to polymer density or percent crystallinity for polymers selected at densities less than about 0.89 g/cm$^3$. Generally, the lower the density, the lower the permanent set as indicated in FIG. 1. For materials made from a homogeneously branched substantially linear ethylene polymer having a density less than about 0.89 g/cm$^3$, the percent permanent set is less than or equal to about 20% (i.e., the recovery is at least about 80%).

FIG. 1 also indicates at densities greater than about 0.89 g/cm$^3$ up to about 0.92 g/cm$^3$, the slope of the curve that describe the relationship between density and elasticity is surprisingly flat. Above 0.92 g/cm$^3$, as polymer density is further increased, the slope of the curve is steep indicating the type of predictable density/elasticity relationship generally known in the art. The density/elasticity relationship of substantially linear ethylene polymers is also characterized by a steep slope in the preferred density range of less than about 0.89 g/cm$^3$. As such, FIG. 1 is suitably labeled to indicate three relatively discrete regions of elasticity; the preferred range is assigned the "Elastic Region", the intermediate range where the slope is unexceptedly flat is assigned the "Elasticity Transition Zone", and the final range is assigned the "Nonelastic Region".

Figure 2:
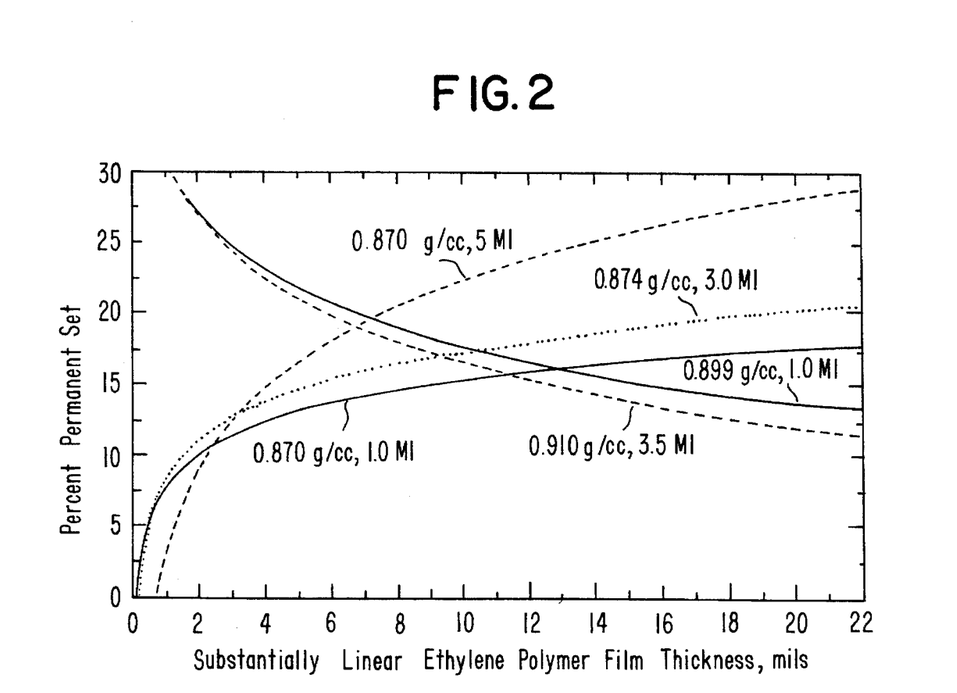
FIG. 2 graphically displays the logarithmic curve fit for the percent permanent set of film made from both elastic substantially linear ethylene polymers of the present invention and higher density substantially linear ethylene polymers versus film thickness.

Table 1 indicates with respect to comparative examples 7, 8, 13 and 14 that film prepared from a homogeneously branched substantially linear ethylene polymer having a density within the Elastic Transition Zone shows less elasticity than heterogeneously branched linear ethylene polymers at equivalent or lower density and crystallinity. Moreover, Table 1 also indicates that the preferred homogeneously branched substantially linear ethylene polymers disclosed herein show superior elasticity and stretchability in contradistinction to other homogeneously branched substantially ethylene polymers due to the lower density and crystallinity of the preferred materials. Surprisingly, as illustrated in FIG. 2, preferred homogeneously branched substantially linear ethylene polymers are further distinguished from other homogeneously branched substantially ethylene polymers due to their tendency to show enhanced elasticity as film thickness is reduced whereas other homogeneously branched substantially linear ethylene polymers where the polymer density is greater than about 0.89 g/cm$^3$ will show less elasticity at reduced film thicknesses.

Where the elasticity of the unique polymers used in the present invention varies with respect to the thickness of the material, thicknesses less than about 22 mils, preferably from about 0.1 mils to about 20 mils, and more preferably, from about 0.4 mils to about 15 mils are considered to be within the purview of this invention.

For the novel elastic materials disclosed herein, the melt index of the substantially linear polymer can be widely varied, with little impact on elasticity. This allows more design flexibility for elastic composites and finished articles because the strength and retractive force of the elastic material can be changed independently of its elasticity. For example, the tensile strength properties of an elastic film can be changed by changing the polymer's melt index (decreasing the melt index increases the tensile strength properties), rather than by changing the thickness of the film, thus permitting a better optimization of the "hand" (i.e., feel) of an elastic composite fabric with the desired elastic/strength performance of the composite fabric. The melt index of the substantially linear ethylene polymers disclosed herein is limited in traditionally ways as requirements respecting specific extrusion processes. As examples, extrusion coating and injection molding processes typically require high melt indices to avoid excessive extrusion pressures and polymer shearing as well as to provide adequate melt flow characteristics, while blown film processes generally requirement lower melt indices to achieve adequate bubble stability.

Elastic Material Fabrication

The films, coatings, and sheets of the present invention may be fabricated by any polyolefin extrusion technique known in the art, including blown bubble processes, cast extrusion, injection molding processes, thermoforming processes, extrusion coating processes, profile extrusion, and sheet extrusion processes. Simple blown bubble film processes are described, for example, in *The Encyclopedia of Chemical Technology*, Kirk-Othmer, Third Edition, John Wiley & Sons, New York, 1981, Vol. 16, pp. 416–417 and Vol. 18, pp. 191–192. The cast extrusion method is described, for example, in Modern Plastics Mid-October 1989 Encyclopedia Issue, Volume 66, Number 11, pages 256 to 257. Injection molding, thermoforming, extrusion coating, profile extrusion, and sheet extrusion processes are described, for example, in Plastics Materials and Processes, Seymour S. Schwartz and Sidney H. Goodman, Van Nostrand Reinhold Company, New York, 1982, pp. 527–563, pp. 632–647, and pp. 596–602. The strips, tapes and ribbons of the present invention can be prepared by the primary extrusion process itself or by known post-extrusion slitting, cutting or stamping techniques. Profile extrusion is an example of a primary extrusion process that is particularly suited to the preparation of tapes, bands, ribbons and the like.

The elastic materials of the present invention can also be rendered pervious or "breathable" by any method well known in the art including by apperturing, slitting, microperforating, mixing with fibers or foams, or the like and combinations thereof. Examples of such methods include, U.S. Pat. Nos. 3,156,242 by Crowe, Jr., 3,881,489 by Hartwell, 3,989,867 by Sisson and 5,085,654 by Buell, the disclosures of all of which are incorporate herein by reference.

Fabricated Composite Articles

Fabricated articles which can be made using the novel elastic materials disclosed herein include composite fabric articles (e.g., disposable incontinence garments and diapers) that are comprised of one or more elastic component or portion. For example, elastic components are commonly present in diaper waist band portions to prevent the diaper from falling and leg band portions to prevent leakage (as shown in U.S. Pat. No. 4,381,781 (Sciaraffa), the disclosure of which is incorporated herein by reference). Often, the elastic component promotes better form fitting and/or fastening systems for a good combination of comfort and security. The novel elastic materials disclosed herein can also produce fabric composite structures which combine elasticity with breathability by utilization a technique that renders the elastic material pervious or "breathable" such as suggested by Lippert et al. in U.S. Pat. No. 4,861,652 and indicated above.

The novel elastic materials disclosed herein can also be used in various structures as described in U.S. Pat. No. 2,957,512 (Wade), the disclosure of which is incorporated herein by reference. For example, layer 50 of the structure described in '512 Patent (i.e., the elastic component) can be replaced with the novel elastic materials, especially where flat, pleated, creped, etc., nonelastic materials are made into elastic or semi-elastic structures. Attachment of the novel elastic materials to nonelastic or less-elastic materials can be done with heat bonding or with adhesives. Gathered or shirred elastic composite materials can be produced from the new elastic material described herein and nonelastic components by pleating the nonelastic component (as described in '512 patent) prior to attachment, prestretching the elastic component prior to attachment, or heat shrinking the elastic component after attachment.

The recovery after heat shrinking can be further enhanced by effectuating a high degree of orientation into the elastic material during fabrication. Significant orientation can be accomplished by the utilization of various known techniques such as high blow-up blown film fabrication, tenter flaming of cast films and "double bubble" or "trapped bubble" blown film fabrication as described in copending application Ser. No. 08/055,063, filed Apr. 28, 1993, disclosure of which is incorporated herein by reference.

The novel elastic materials described herein can also be used make other novel structures. For example, U.S. Pat. No. 4,801,482 (Goggans), the disclosure of which is incorporated herein by reference, discloses an elastic sheet (12) which can now be made with the novel materials described herein.

The novel elastic materials described herein can also be used to make breathable portion or breathable elastic composite materials. For example, U.S. Pat. No. 5,085,654 (Buell) discloses a leg band (15) with a breathable portion 45, a breathable topsheet (26), a breathable backsheet (25), elastic elements (31 and 64), a breathable element (54), and a breathable sub-element (96) all or any combination of which can now be made with the elastic materials disclosed herein in either pervious or impervious forms.

The novel elastic materials disclosed herein also have adjustable stretchability and elasticity that can be achieved by specific combinations of elastic materials and less-elastic material and/or by adjusting the polymer density or by specific combination of different substantially linear ethylene polymers, which enables design flexibility for variable stretchability or retractive force in the same garment, as described for example in U.S. Pat. No. 5,196,000 (Clear et al.), the disclosure of which is incorporated herein by reference.

U.S. Pat. No. 5,037,416 (Allen et al.), the disclosure of which is incorporated herein by reference, describes the advantages of a form fitting top sheet by using elastic ribbons (member 12) and an elastic backsheet (member 16). Pervious novel elastic materials described herein could serve the function of member 12 and impervious elastics materials of this invention could function as member 16, or disclosed elastic materials could be used in an elastic composite fabric form.

In U.S. Pat. No. 4,981,747 (Morman), the novel elastic materials disclosed herein can be substituted for elastic sheets 12, 122 and 232 to construct an elastic composite material which includes a reversibly necked material.

Elastic panels, elements, portions or the like can also be made from the novel elastic materials disclosed herein, and can be used, for example, as members 18, 20, 24, and/or 26 of U.S. Pat. No. 4,940,464 (Van Gompel), the disclosure of which is incorporated herein by reference. The novel elastic materials described herein can also be used, for example, as elastic composite side panels (e.g., layer) or as elastic ribbons 42 and/or 44.

EXAMPLES

The following examples illustrate some of the particular embodiments of the present invention, but the following should not be construed to mean the invention is limited to the particular embodiments shown.

Inventive Examples 1–6 and Comparative Examples 7–14

Table 1 indicates the melting point, crystallinity and percent permanent set for the various films. Except comparative examples 13 and 14, all examples are comprised of a substantially linear ethylene/1-octene copolymer produced by a continuous solution polymerization in the presence of a contrained geometry catalsyt system as described in U.S. Pat. No. 5,272,236 and U.S. Pat. No. 5,278,272. Comparative examples 13 and 14 are heterogeneous branched linear low density ethylene polymers.

Whereas examples 1–14 are cast films, Inventive Examples 15, 16 and 17 are blown bubble elastic films. Inventive Example 17 comprises 85 weight percent Inventive Example 1 and 15 weight percent of a low density polyethylene resin with a 0.7 g/10 min. Melt Index and a 0.9235 g/cm$^3$ density blended by tumble blending.

A three-extruder cast coextrusion film line equipped with a 20/60/20 feedblock design and a slot die is used to fabricate the films of Examples 1–14. The cast film line extruder diameters are 2½, 3½ and 2 inches (6.4, 8.9 and 5.1 cm), respectively, and the die width measures 76 cm with a 20-mil manual die gap. The fabrications consist of maintaining melt temperatures at about 274 C to prepare 1.5 mil and 3.0 mil film samples.

Examples 15, 16 and 17 are blown film samples fabricated using a 2.5 inch (6.35 cm) diameter Gloucester extruder equipped with a 6 inch (15.2 cm) annular die. Output rate for the fabrication is maintained at 120 lb/hr. (54.5 kg/hr.) with the melt temperature at 440 F (227 C) and the blow-up ratio (BUR) at 2.5:1 to prepare from about 0.75 mil to about 2.5 mil layflat film.

The melting point and crystallinity of the resultant films are determined using differential scanning calorimetry (DSC) analysis where 292 J/g is taken as the heat of fusion for a 100% crystallinity polymer film.

The percent permanent set is obtained by cutting the films into 2.5 cm×15 cm strips and testing each film on an Instron tensiometer equipped with a small plastic jaw on the crosshead (the jaw has a weight of about six grams) and a 500 gram load cell. The jaws are set 1 inch (2.54 cm) apart. The cross head speed is set at 5 inches/minute (12.7 cm/minute). A single film specimen is loaded into the Instron jaws for testing. The film is allowed to return to the original Instron setting (where the jaws are again 1 inch apart) and the film is again pulled. At the point where the film begins to provide stress resistance, the strain is recorded and the percent permanent set is calculated. In one example, a film pulled for the second time did not provide stress resistance (i.e., pull a load) until it had traveled 0.2 inches (0.5 cm). Thus, the percent permanent set is calculated as 20%, i.e., the percent of elongation at which the film begins to provide stress resistance. The numerical difference between the percent permanent set and 100% is known as the percent elastic recovery. Thus, a film having a permanent set of 20% will have a 80% elastic recovery. After recording percent permanent set, the film is pulled to 100% elongation. The film pulling process is repeated five times for each determination and repeated at least twice, average and recorded as percent permanent set at the beginning of the fifth pull.

Examples 1–6 are all easily made into film and have less permanent set (more elasticity) than comparative examples 7–14 due to their lower density and crystallinity. Surprisingly, although comparative examples 7 and 8 show a substantially lower density than comparative examples 13 and 14, the percent permanent set values for comparative examples 7 and 8 are either equivalent to or inferior to that of the heterogeneously branched linear ethylene polymer. The elastic response of substantially linear ethylene polymers in this range of densities (0.89 $g/cm^3$ to about 0.92 $g/cm^3$) is surprisingly flat and cannot be confidently predicted from polymer density. At all densities above about 0.89 $g/cm^3$, Table 1 indicates the materials are nonelastic (permanent set is greater than 20 percent, or recovery is less than 80 percent).

Table 1 also indicates that the elastic materials described herein tend to show enhanced elasticity as film thickness is reduced while substantially linear ethylene polymers above about 0.89 $g/cm^3$ density tend to show less or unchanged elasticity at reduced film thicknesses.

TABLE 1

| Examples* | Melt Index g/10 min. | Density g/cc | MWD | I10/I2 Ratio | DSC Melting Point, C. 1st Heat | 2nd Heat | % Crystallinity 1st Heat | 2nd Heat | Film Thickness (mils) | 5th Pull % Permanent Set | % Standard Deviation |
|---|---|---|---|---|---|---|---|---|---|---|---|
| Inventive Example | | | | | | | | | | | |
| 1 | 1.0 | 0.870 | 2.04 | 7.4 | 55.5 | 54.0 | 5.8 | 9.7 | 1.5 | 9.1 | 2.6 |
| 2 | | | | | | | | | 3.0 | 11.4 | 1.0 |
| 3 | 3.0 | 0.874 | 2.01 | 7.4 | 55.5 | 60.6 | 8.3 | 13.8 | 1.5 | 9.9 | 3.6 |
| 4 | | | | | | | | | 3.0 | 12.6 | 1.5 |
| 5 | 5.0 | 0.870 | 2.00 | 7.3 | 55.8 | 56.9 | 4.7 | 12.1 | 1.5 | 6.5 | 1.7 |
| 6 | | | | | | | | | 3.0 | 12.3 | 0.8 |
| Comparative Example | | | | | | | | | | | |
| 7 | 1.0 | 0.899 | 2.17 | 8.6 | 92.9 | 94.0 | 18.3 | 31.0 | 1.5 | 28.7 | 1.7 |
| 8 | | | | | | | | | 3.0 | 24.7 | 0.5 |
| 9 | 3.5 | 0.911 | 2.14 | 7.0 | 104.0 | 104.2 | 27.5 | 40.5 | 1.5 | 28.7 | 1.5 |
| 10 | | | | | | | | | 3.0 | 24.3 | 1.2 |
| 11 | 2.5 | 0.935 | 2.11 | 9.5 | 122.6 | 123.6 | 51.1 | 61.2 | 1.5 | 61.1 | 2.5 |
| 12 | | | | | | | | | 3.0 | 60.2 | 3.2 |
| 13 | 2.3 | 0.917 | ND | 7.4 | 123.6 | 121.8 | 31.6 | 45.2 | 1.5 | 27.3 | 1.5 |
| 14 | | | | | | | | | 3.0 | 29.5 | 0.9 |
| Inventive Example | | | | | | | | | | | |
| 15 | 1.0 | 0.870 | | 7.4 | ND | ND | ND | ND | 1.5 | 6.6 | 2.2 |
| 16 | | | | | | | | | 4.0 | 12.3 | 1.5 |
| 17 | — | — | | — | ND | ND | ND | ND | 5.0 | 12.8 | 0.5 |

*Permanent set and standard deviation are taken as average of machine and cross direction determinations. Melt points and %crystallinity are determined on films at 3 mils thickness.
ND = not determined.

Inventive Examples 15–17

Inventive Examples 15 and 16 indicate that there is no substantial difference between fabricating the elastic materials disclosed herein by cast extrusion or by blown film extrusion. Inventive Example 17 shows admixtures comprised of up to 15 weight percent of other polyolefin (0.7 MI, 0.9235 density low density polyethylene) does not adversely affect the excellent elasticity of the elastic materials of the present invention.

Elastic Composite Material Example

Figure 3:
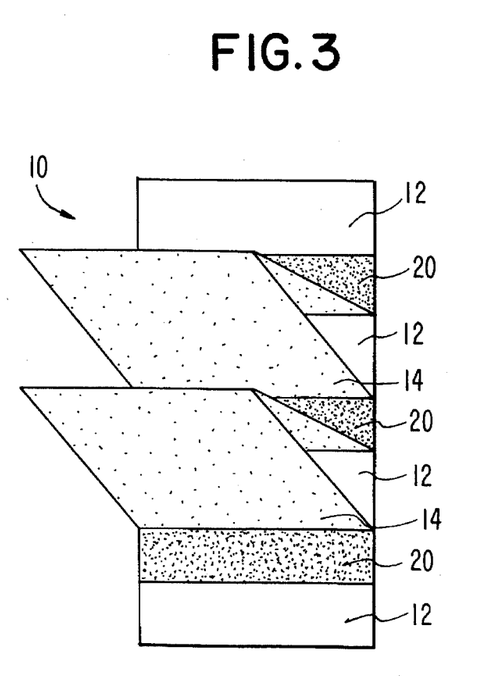
FIG. 3 is a perspective view of an elastic composite material of the present invention with enhanced stretchability comprising an elastic material layer attached to a nonelastic material layer; the elastic material layer is disclosed herein.
Figure 3A:
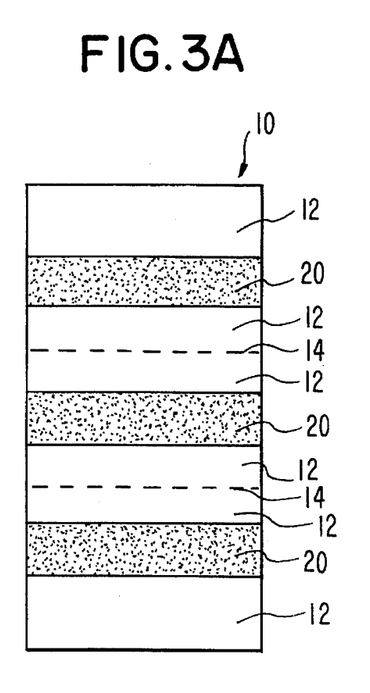
FIG. 3A is a top plan view of the inventive elastic composite material of FIG. 3.

In another investigation, an elastic composite structure 10 depicted in FIGS. 3 and 3A is constructed according to the description in U.S. Pat. No. 2,957,512. In this investigation, Inventive Example 6 herein is substituted for layer 50 in FIG. 9 of '512 patent and a lab-produced nonwoven is substituted for layer 59 in FIG. 9 of '512patent. Fibers for the lab-produced nonven is prepared from ASPUN* 6811A fiber grade resin (a heterogeneously branched ethylene/1-octene copolymer having a density of 0.941 g/cm$^3$ and a melt index of 27 g/10 min. and is supplied by The Dow Chemical Company) and spunbond by Polybond, Inc. to 1.5 oz/yd$^2$). Whereas layer 50 in FIG. 9 of '512 patent constitutes the elastic layer, layer 12 herein in FIGS. 3 and 3A consititutes the elastic layer, and whereas layer 59 in FIG. 9 of '512 is the nonelastic layer, layer 14 herein FIGS. 3 and 3A is the nonelastic layer. The percent permanent set is 68% for nonelastic layer 14 herein. After spunbonding, the fibrous nonwoven web is further processed by well known thermal bonding calendering where the calender consists of a 5" diameter smooth bottom roll and 5" diameter diamond embossed top roll. Calendering conditions include a 400 psi nip pressure, a roll speed of ~4 rpm, and a ~200 F roll temperature. An elastic composite material 10 is formed by cutting or sizing the calendered nonelastic nonwoven sheet into a 2×12 inch strip and cutting the 3 mil film of Inventive Example 6 into a 2×6 inch strip. The nonelastic nonwoven 14 is then evenly pleated to create two evenly spaced folds and then at least one ply of unstretched Inventive Example 6 elastic film is placed on top of nonwoven. The construction is then sandwiched between Mylar™ polyester film supplied by E.I. Du Pont de Nemours and Company to prevent sticking to the heated rolls and inverted such that the elastic film is oriented on the bottom of the construction. The construction is then passed through the heated nip of the calender to melt bonded the Inventive elastic film to the nonelastic nonwoven and create three melt bond areas 20. The resultant elastic composite fabric structure 10 exhibits good stretchability where stretch-to-end performance is 139 percent and percent elongation by Instron tensiometer determination is 600.

We claim:

1. An elastic material having a percent recovery of at least about 80 percent and a thickness of less than about 22 mils comprising at least one homogeneously branched substantially linear ethylene polymer characterized as having:

a) a melt flow ratio, $I_{10}/I_2$, $\geq 5.63$, b) a molecular weight distribution, $M_w/M_n$, defined by the equation:

$$M_w/M_n \leq (I_{10}/I_2) - 4.63,$$

c) a critical shear rate at onset of surface melt fracture of at least 50 percent greater than the critical shear rate at the onset of surface melt fracture of a linear ethylene polymer having about the same $I_2$ and $M_w/M_n$, and d) a density less than about 0.89 g/cm$^3$, wherein the elastic material is selected from the group consisting of films, strips, coatings, tapes, webs, ribbons, bands and sheets.

2. The elastic material of claim 1 wherein the $M_w/M_n$ of the homogeneously branched substantially linear ethylene polymer is less than about 3.5.

3. The elastic material of claim 1 wherein the $M_w/M_n$ of the homogeneously branched substantially linear ethylene polymer is from about 1.5 to about 2.5.

4. The elastic material of claim 1 wherein the $I_{10}/I_2$ of the ethylene polymer is at least about 6.

5. The elastic material of claim 4 wherein the $I_{10}/I_2$ of the ethylene polymer is at least about 7.

6. The elastic material of claim 1 wherein the ethylene polymer is an interpolymer of ethylene with at least one $C_3$–$C_{20}$ α-olefin.

7. The elastic material of claim 1 wherein the ethylene polymer is a copolymer of ethylene with a $C_3$–$C_{20}$ α-olefin.

8. The elastic material of claim 1 wherein the ethylene polymer is a copolymer of ethylene with 1-butene, 1-hexene, 4-methyl-1-pentene or 1-octene.

9. The elastic material of claim 8 wherein the ethylene polymer is a copolymer of ethylene with 1-octene.

10. The elastic material of claim 9 wherein the density of the ethylene polymer is from about 0.85 to about 0.89 g/cm$^3$.

11. The elastic material defined in claim 1 wherein the elastic material is a film.

12. An elastic composite material comprising at least one elastic material having a percent recovery of at least about 80 percent and a thickness of less than about 22 mils, wherein the elastic material comprises at least one homogeneously branched substantially linear ethylene polymer characterized as having:

a) a melt flow ratio, $I_{10}/I_2$, $\geq 5.63$, b) a molecular weight distribution, $M_w/M_n$, defined by the equation:

$$M_w/M_n \leq (I_{10}/I_2) - 4.63,$$

c) a critical shear rate at onset of surface melt fracture of at least 50 percent greater than the critical shear rate at the onset of surface melt fracture of a linear ethylene polymer having about the same $I_2$ and $M_w/M_n$, and d) a density less than about 0.89 g/cm$^3$, wherein the elastic material is selected from the group consisting of films, strips, coatings, tapes, webs, ribbons, bands and sheets.

13. A fabricated composite article comprising at least one elastic material having a percent recovery of at least about 80 percent and a thickness of less than about 22 mils, wherein the elastic material comprises at least one homogeneously branched substantially linear ethylene polymer characterized as having:

a) a melt flow ratio, $I_{10}/I_2$, $\geq 5.63$, b) a molecular weight distribution, $M_w/M_n$, defined by the equation:

$$M_w/M_n \leq (I_{10}/I_2) - 4.63,$$

c) a critical shear rate at onset of surface melt fracture of at least 50 percent greater than the critical shear rate at the onset of surface melt fracture of a linear ethylene polymer having about the same $I_2$ and $M_w/M_n$, and d) a density less than about 0.89 g/cm$^3$, wherein the elastic material is selected from the group consisting of films, strips, coatings, tapes, webs, ribbons, bands and sheets.

14. A fabricated composite article comprising at least one elastic composite material, wherein the elastic composite material comprises at least one elastic material having a percent recovery of at least about 80 percent and a thickness of less than about 22 mils, wherein the elastic material comprises at least one homogeneously branched substantially linear ethylene polymer characterized as having:

a) a melt flow ratio, $I_{10}/I_2$, $\geq 5.63$, b) a molecular weight distribution, $M_w/M_n$, defined by the equation:

$$M_w/M_n \leq (I_{10}/I_2) - 4.63,$$

c) a critical shear rate at onset of surface melt fracture of at least 50 percent greater than the critical shear rate at the onset of surface melt fracture of a linear ethylene polymer having about the same $I_2$ and $M_w/M_n$, and d) a density less than about 0.89 g/cm³, wherein the elastic material is selected from the group consisting of films, strips, coatings, tapes, webs, ribbons, bands and sheets.

15. An elastic material having a percent recovery of at least about 80 percent and a thickness of less than about 22 mils consisting essentially of a homogeneously branched substantially linear ethylene polymer characterized as having:

a) a melt flow ratio, $I_{10}/I_2$, $\geq 5.63$, b) a molecular weight distribution, $M_w/M_n$, defined by the equation:

$$M_w/M_n \leq (I_{10}/I_2) - 4.63,$$

c) a critical shear rate at onset of surface melt fracture of at least 50 percent greater than the critical shear rate at the onset of surface melt fracture of a linear ethylene polymer having about the same $I_2$ and $M_w/M_n$, and d) a density less than about 0.89 g/cm³, wherein the elastic material is selected from the group consisting of films, strips, coatings, tapes, webs, ribbons, bands and sheets.

* * * * *